US00PP29782P2

(12) United States Plant Patent
Smith

(10) Patent No.: US PP29,782 P2
(45) Date of Patent: Oct. 30, 2018

(54) ***CHRYSANTHEMUM* PLANT NAMED 'CIFZ0042'**

(50) Latin Name: ***Chrysanthemum* x *morifolium***
Varietal Denomination: CIFZ0042

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,486

(22) Filed: Jan. 20, 2017

(51) Int. Cl.
*A01H 5/02* (2018.01)

(52) U.S. Cl.
USPC ..... Plt./288

(58) Field of Classification Search
USPC ..... Plt./288, 289, 294
CPC ..... A01H 5/0255; A01H 5/025; A01H 5/02; A01H 5/00; A01H 6/1424; A01H 6/14
See application file for complete search history.

(56) References Cited

PUBLICATIONS

Broertjes. Mutation Breeding of *Chrysanthemums*. Euphytica 15 (1966): 156-162. (Year: 1966).*

Lucas Greenhouses Finished Catalog 2017-2018, Issuu published on Dec. 20, 2016, retrieved on Feb. 23, 2018, retrieved from the Internet at https://issuu.com/lucasgreenhouses/docs/full_proof_-_12.21_-_reduced_size, 2 cover pages, 111, 138-141. (Year: 2016).*

* cited by examiner

*Primary Examiner* — June Hwu
(74) *Attorney, Agent, or Firm* — Dale Skalla

(57) ABSTRACT

A new garden type *Chrysanthemum* plant named 'CIFZ0042' particularly distinguished by the small size white decorative flowers, large size plant with round sphere plant habit and a natural season response in mid-late October.

1 Drawing Sheet

Latin name of the genus and species of the plant claimed: *Chrysanthemum* x *morifolium*.
Varietal denomination: 'CIFZ0042'.

BACKGROUND OF THE NEW PLANT

The present invention comprises a new *Chrysanthemum*, botanically known as *Chrysanthemum* x *morifolium*, and hereinafter referred to by the variety name 'CIFZ0042'.

'CIFZ0042' is a product of a planned breeding program. The new cultivar has small size white decorative flower, large size plant with round sphere plant habit and a natural season response in mid-late October.

'CIFZ0042' originated from a mutation: Stock x-rayed at 1750 RAD in October of 2014. Single cutting sport from the stock.

The female parent was 'Rhonda Pink'.

Compared to the female parent, 'CIFZ0042' has:

1) Similar flower type and size but white not light lavender/pink color like the sport parent
2) Blackcloth is similar and natural season response is a day or two faster than the sport parent
3) Similar plant habit and slightly smaller plant size than the sport parent No male parent The first act of asexual reproduction of 'CIFZ0042' was accomplished when vegetative stem tip cuttings were propagated from the initial selection, this initial selection took place on Mar. 12, 2015 in Gilroy, Calif.

BRIEF SUMMARY OF INVENTION

Horticultural examination of plants grown from cuttings of the plant initiated in April, 2015 in Gilroy, Calif., and continuing thereafter, has demonstrated that the combination of characteristics as herein disclosed for 'CIFZ0042' are firmly fixed and are retained through successive generations of asexual reproduction.

'CIFZ0042' has not been observed under all possible environmental conditions. The phenotype may vary significantly with variations in environment such as temperature, light intensity and day length.

'CIFZ0042' has not been made publicly available prior to the effective filing date of this application, notwithstanding any disclosure that may have been made less than one year prior to the effective filing date of this application by the inventor or another who obtained 'CIFZ0042' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0042' with colors being as true as possible with an illustration of this type.

Figure 1:
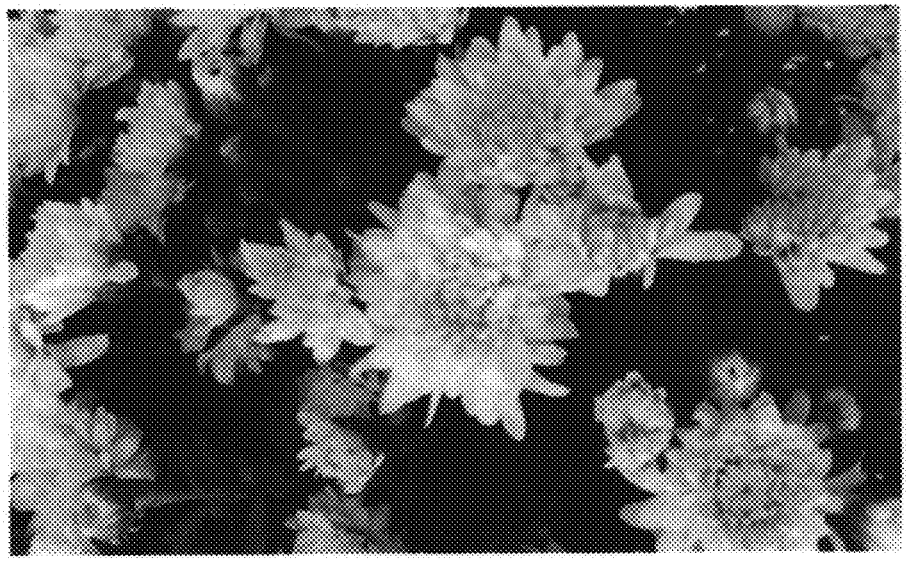
Figure 2:
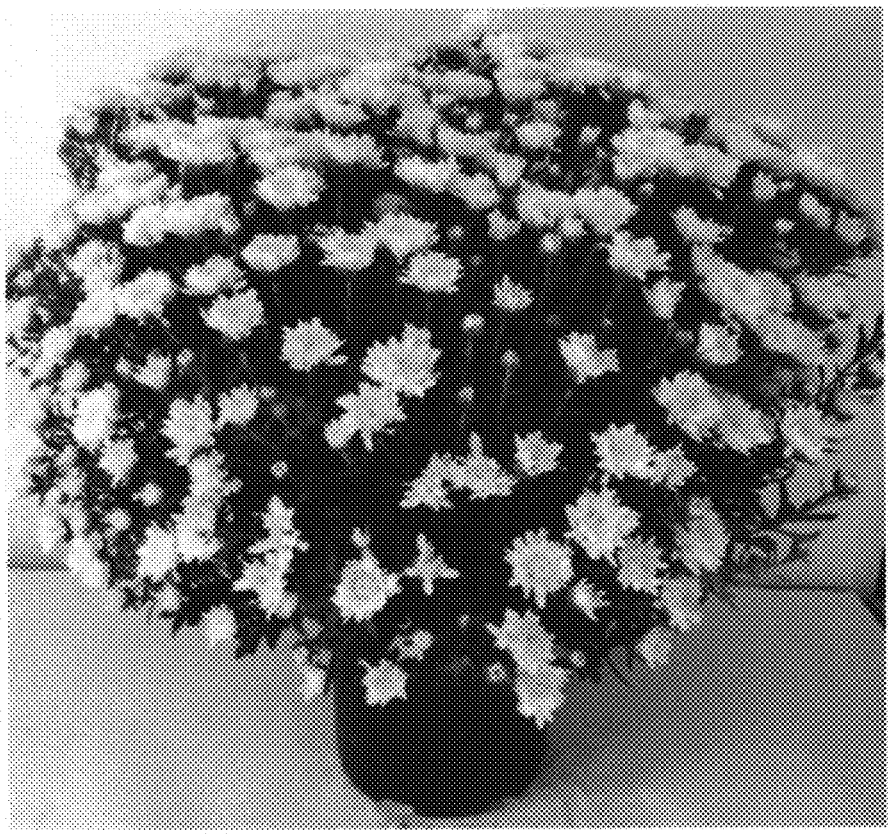

The photographic drawings shown in FIG. 1 is a close-up view of the flowers of the new variety and in FIG. 2 is a flowering plant from an outdoor trial.

The aforementioned photographs: FIG. 1, as well as FIG. 2, were taken in October 2016 both showing a plant from the same natural outdoor trial in Gilroy, Calif.

These plants were about 18 weeks of age. One rooted cutting per pot had been planted in a one gallon pot, not pinched in week 22. Plants started flowering end of September.

DETAILED BOTANICAL DESCRIPTION

The measurements were taken in Gilroy, Calif. in October 2016 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0042' AND 'Yomildred' :

| | 'CIFZ0042' | 'Yomildred', U.S. Plant Pat. No. 21,187 |
|---|---|---|
| Flowering response (blackcloth): | 10 days slower | 10 days faster |
| Flowering response (natural): | 1 week slower | 1 week faster |
| Flower color: | More creamy white color | More pure white color |
| Flower size: | Bit smaller flower | Bit bigger flower |
| Plant habit or size: | Relatively less plant width and therefore more sphere/less mound plant habit compared to 'Yomildred' | Relatively wider plant and therefore less sphere/more mound plant habit compared to 'CIFZ0042' |

TABLE 2

DIFFERENCES BETWEEN THE NEW VARIETY 'CIFZ0042' AND 'Staviski White'

| | 'CIFZ0042' | 'Staviski White', U.S. Plant Pat. No. 21,825 |
|---|---|---|
| Flowering response (blackcloth): | 1 week slower | 1 week faster |
| Flowering response (natural): | 2 days faster | 2 days slower |
| Frost tolerance: | Frost tolerant | Not frost tolerant |
| Flower shape: | Less disc florets | More disc florets |
| Plant habit or size: | Larger plant size | Smaller plant size |

Plant:

*Form, growth and habit.*—Herbaceous garden-type, stems upright and outwardly spreading, freely branching, strong and moderately vigorous growth habit.

*Plant height (above soil).*—19-25 cm.

*Plant height (inflorescence included).*—23-28 cm.

*Plant width.*—44-48 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137B.

*Immature leaf, color lower surface.*—RHS 137C.

*Mature leaf, color, upper surface.*—RHS 137A.

*Mature leaf, color lower surface.*—RHS 137C.

*Length.*—4.1-4.6 cm.

*Width.*—2.5-3.2 cm.

*Shape.*—Ovate.

*Base shape.*—Attenuate.

*Apex shape.*—Acute.

*Margin.*—3 main lobes, irregularly serrated.

*Texture, upper surface.*—Bifid hairs.

*Texture, lower surface.*—Bifid hairs.

*Color of veins, upper surface.*—RHS 138A.

*Color of veins, lower surface.*—RHS 137C.

*Pattern of veining.*—Palmate.

*Petiole color.*—RHS 138B.

*Petiole length.*—1.1-1.9 cm.

*Diameter.*—0.15-0.2 cm.

*Texture.*—Covered with bifid hairs.

Stem:

*Quantity of main branches per plant.*—13-15.

*Color of stem.*—RHS 138B.

*Length of stem.*—10-13 cm.

*Diameter.*—0.3-0.5 cm.

*Length of internodes.*—0.8-1.8 cm.

*Texture.*—Bifid hairs.

*Color of peduncle.*—RHS 138B.

*Length of peduncle.*—7-11 cm.

*Peduncle diameter.*—0.15 cm.

*Texture.*—Bifid hairs.

Inflorescence:

*Type.*—Compositae, solitary, decorative-type inflorescences borne terminally above foliage, ray florets arranged on a capitulum.

*Quantity of short days to flowering (response time).*—Approximately 7 weeks.

*Natural season flowering.*—Mid-late October.

*Quantity of inflorescences per plant.*—200-250, with buds in various stages of development.

*Lastingness of individual blooms on the plant.*—About six weeks from first color.

*Fragrance.*—Slightly spicy.

Bud (when showing color):

*Color.*—Closest to RHS 10B.

*Length.*—1.0-1.3 cm.

*Width.*—0.8-1.0 cm.

*Shape.*—Oblate.

Immature inflorescence:

*Diameter.*—1.8-2.4 cm.

*Color of ray florets, upper surface.*—In case of not expanded whorl: RHS 2C, RHS 10D when expanded.

*Color of ray florets, lower surface.*—RHS 4C.

Mature inflorescence:

*Diameter.*—3.1-3.7 cm.

*Depth.*—1.8-2.1 cm.

*Total diameter of disc.*—Very small; not visible as covered by the many rays.

*Receptacle color.*—RHS 145B.

*Receptacle height.*—0.4 cm.

*Receptacle diameter.*—1.1-1.4 cm.

Ray florets:

*Average quantity of florets.*—Between 150 and 180 in many whorls.

*Color of florets, upper surface.*—RHS 155D; RHS 10C for inner whorls.

*Color inner surface.*—RHS 155D.

*Length.*—1.0-1.2 cm.

*Width/diameter.*—0.25-4.0 cm.
*Shape.*—Oblong to elliptical.
*Apex shape.*—Most often emarginated or praemorse.
*Base shape.*—Attenuate.
*Margin.*—Entire.
*Texture, upper surface.*—Smooth.
*Lower surface.*—Smooth.

Disc florets: None present.

Phyllaries:
*Quantity.*—Approximately 40.
*Color, upper surface.*—RHS 137B.
*Color, lower surface.*—RHS 137C.
*Length.*—0.6-0.7 cm.
*Width.*—0.15-2.0.
*Shape.*—Lanceolate.
*Apex shape.*—Acute.
*Base.*—Fused.
*Margins.*—Entire, some with papery edges.
*Texture, upper surface.*—Glabrous.
*Texture, lower surface.*—Bifid hairs.

Reproductive organs:
*Pistil.*—One on disc florets.
*Length.*—0.5-0.6 cm.
*Style color.*—RHS 1C.
*Style length.*—0.35-0.45 cm.
*Stigma color.*—RHS 7D.
*Stigma shape.*—Bi-parted.
*Ovary color.*—RHS 145C.
*Ovary length.*—0.15 cm.
*Ovary width.*—0.1 cm.

Androecium:
*Stamens.*—4.
*Color of filaments.*—RHS 155C.
*Length filaments.*—0.15-0.25 cm.
*Anther color.*—RHS 6A.
*Anther length.*—0.1 cm.
*Anther shape.*—Oblong.
*Color of pollen.*—RHS 15C.
*Pollen amount.*—Sparse.
*Fertility/seed set.*—Has not been determined to date.
*Disease/pest resistance.*—Has not been determined to date.
*Cold tolerance.*—Frost Tolerant.

What is claimed is:

1. A new and distinct variety of *Chrysanthemum* plant named 'CIFZ0042' substantially as illustrated and described herein.

* * * * *